US011844344B2

(12) United States Patent
McEntire et al.

(10) Patent No.: US 11,844,344 B2
(45) Date of Patent: *Dec. 19, 2023

(54) SYSTEMS AND METHODS FOR RAPID INACTIVATION OF SARS-COV-2 BY SILICON NITRIDE AND ALUMINUM NITRIDE

(71) Applicant: SINTX TECHNOLOGIES, INC., Salt Lake City, UT (US)

(72) Inventors: Bryan J. McEntire, Salt Lake City, UT (US); Ryan M. Bock, Salt Lake City, UT (US); Bhajanjit Singh Bal, Salt Lake City, UT (US)

(73) Assignee: SINTX Technologies, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/230,395

(22) Filed: Apr. 14, 2021

(65) Prior Publication Data
US 2021/0227832 A1 Jul. 29, 2021

Related U.S. Application Data

(63) Continuation-in-part of application No. 16/550,605, filed on Aug. 26, 2019, now Pat. No. 11,192,787.

(60) Provisional application No. 63/045,355, filed on Jun. 29, 2020, provisional application No. 62/727,724, filed on Sep. 6, 2018, provisional application No. 62/800,034, filed on Feb. 1, 2019.

(51) Int. Cl.
*A01N 59/06* (2006.01)
*A01N 59/00* (2006.01)
*A61L 31/16* (2006.01)
*A61L 31/08* (2006.01)
*D06N 3/12* (2006.01)

(52) U.S. Cl.
CPC ............ *A01N 59/06* (2013.01); *A01N 59/00* (2013.01); *A61L 31/088* (2013.01); *A61L 31/16* (2013.01); *D06N 3/128* (2013.01); *A61L 2300/408* (2013.01); *D06N 2211/10* (2013.01); *D06N 2211/103* (2013.01); *D06N 2211/18* (2013.01)

(58) Field of Classification Search
None
See application file for complete search history.

(56) References Cited

U.S. PATENT DOCUMENTS 6,302,913 B1 ‡ 10/2001 Ripamonti ........... A61C 8/0012
623/16.11
7,776,085 B2 ‡ 8/2010 Bernero .................... A61F 2/38
623/2.32
9,925,295 B2 ‡ 3/2018 McEntire .............. C04B 35/597
10,806,831 B2 ‡ 10/2020 McEntire ................. A61L 27/50
2009/0320172 A1* 12/2009 Slate ......................... F41H 1/02
2/2.5
2010/0040655 A1 ‡ 2/2010 Ren ..................... A41D 13/1192
424/402
2013/0236854 A1 ‡ 9/2013 McEntire ............. A61C 8/0013
433/173
2013/0302509 A1 ‡ 11/2013 McEntire ................ A61L 27/54
427/2.24
2016/0339144 A1 ‡ 11/2016 McEntire .............. A61L 27/025
2017/0197014 A1 ‡ 7/2017 McEntire .............. A61L 31/022

FOREIGN PATENT DOCUMENTS

CN 107926975 A ‡ 4/2018
JP 2009526828 A 7/2009
JP 2015516239 A 6/2015
JP 2020019677 A 2/2020
WO WO-2011067005 A1 * 6/2011 ............. A41D 13/11

OTHER PUBLICATIONS

Pezzotti et al.( Rapid inactivation of SARS-CoV-2 by silicon nitride, copper, and aluminum nitride bioRxiv (2020) 1-16, 2020). (Year: 2020).*
Pezzotti et al. (Instantaneous catch-and-kill inactivation of SARS-CoV-2 by nitride ceramics, Clinical and Translational Medicine (2020), 10(6), e212 ). (Year: 2020).*
Lehman et al.( Silicon nitride inactivates SARS-CoV-2 in vitro, bioRxiv (2020) 1-11, 2020). (Year: 2020).*
Adiga et al., Nanoporous membranes for medical and biological applications, 2009, Nanomed Nanobiotechnology, vol. 1, No. 5, pp. 568-581 (Year: 2009).‡
Extended European Search Report issued in corresponding Application No. 19856613.5 dated May 2, 2022, 10 pages.
First Examination Report issued in corresponding Indian Application No. 202137015785, 7 pages.
Office Action issued in related U.S. Appl. No. 17/230,395 dated Oct. 28, 2022, 11 pages.
Office Action issued in related U.S. Appl. No. 17/230,284 dated Oct. 28, 2022, 10 pages.
Pezzotti et al., Rapid Inactivation of SARS-CoV-2 by Silicon Nitride, Copper, and Aluminum Nitride, 2020, 16 pages.
Office Action dated Nov. 25, 2022 in Canadian Application No. 3,109,874, 4 pages.
U.S. Patent and Trademark Office, Final Office Action, U.S. Appl. No. 17/230,284, dated Apr. 6, 2023, 9 pages.
U.S. Patent and Trademark Office, Final Office Action, U.S. Appl. No. 17/230,402, dated Apr. 14, 2023, 11 pages.
IP Australia, Examination Report No. 2 for Standard Patent Application, Application No. 2019336133, dated May 3, 2023, 5 pages.
China National Intellectual Property Administration (CNIPA), First Office Action, Application No. 201980058291.0, Mar. 8, 2023, 18 pages.
Japan Patent Office, Notice of Reasons for Rejection, Application No. 2021-510805, dated Jan. 24, 2023, 5 pages.

* cited by examiner
‡ imported from a related application

*Primary Examiner* — Alton N Pryor
(74) *Attorney, Agent, or Firm* — Polsinelli PC

(57) ABSTRACT

Various embodiments related to systems, methods, and articles for rapid inactivation of SARS-CoV-2 by silicon nitride and aluminum nitride are disclosed herein.

12 Claims, 12 Drawing Sheets

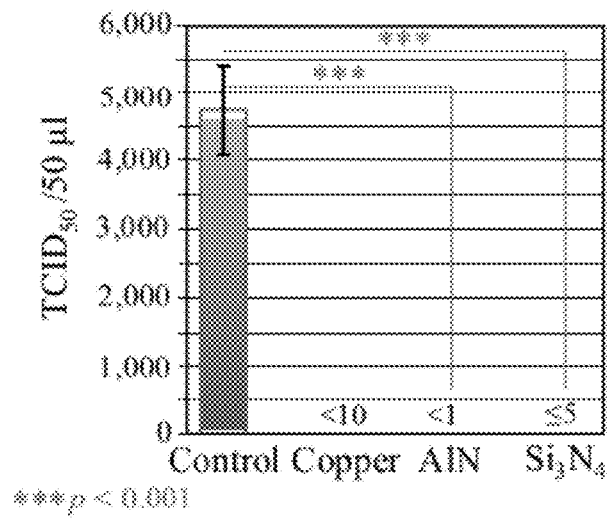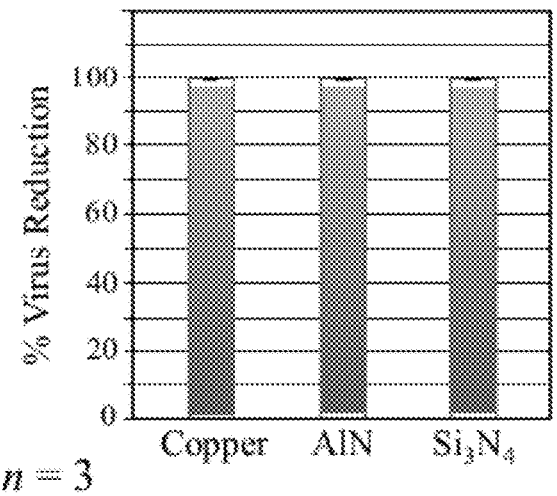
FIG. 1A  FIG. 1B
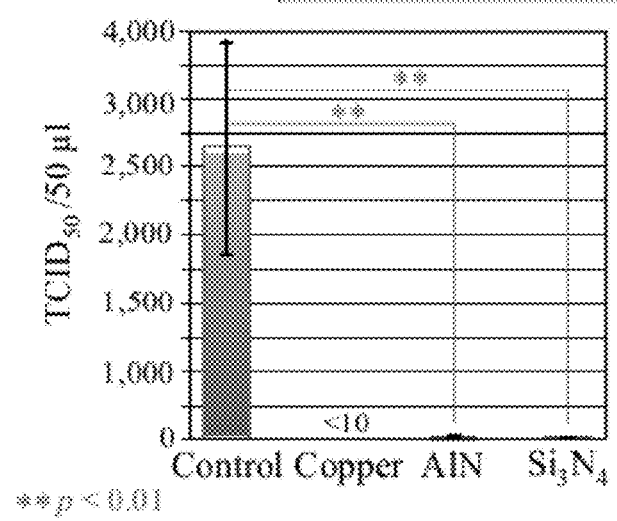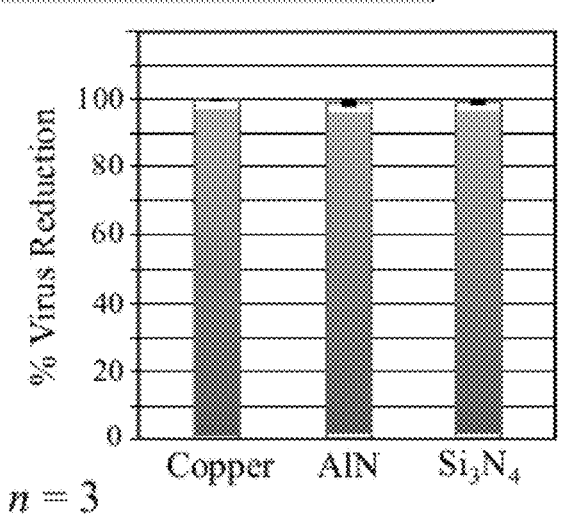
FIG. 1C  FIG. 1D

SYSTEMS AND METHODS FOR RAPID INACTIVATION OF SARS-COV-2 BY SILICON NITRIDE AND ALUMINUM NITRIDE

CROSS-REFERENCE TO RELATED APPLICATIONS

This application is a Continuation-in-Part of U.S. application Ser. No. 16/550,605, filed Aug. 26, 2019 that claims the benefit of U.S. Provisional Applications 62/727,724, filed Sep. 6, 2018 and 62/800,034, filed Feb. 1, 2019. This application also claims the benefit of U.S. Provisional Application No. 63/045,355, filed Jun. 29, 2020. The contents of all of which are entirely incorporated by reference herein.

FIELD

The present disclosure generally relates to rapid inactivation of a virus, and in particular to systems and methods for rapid capture and inactivation of SARS-CoV-2 by silicon nitride and/or aluminum nitride.

BACKGROUND

The novel coronavirus, SARS-CoV-2, has led to a worldwide pandemic and raised interest in the surface-mediated transmission of viral diseases. Respiratory aerosols and droplets, and contaminated surfaces facilitate viral spread from person to person leading to recommendations of social distancing, wearing of masks, hand-washing, and regular surface disinfection. Data suggest that the SARS-CoV-2 virus can remain viable on copper, plastic, steel, and cardboard surfaces for 4-72 hours after contact, and up to 7-days on surgical masks. Viral persistence on these and other materials presents a risk for the social and nosocomial propagation of COVID-19, the disease caused by SARS-CoV-2. Current viral inactivation methods include the surface application of chemicals, such as a combination of ethanol with hydrogen peroxide or sodium hypochlorite. Irradiation of surfaces with ultraviolet light is another virus disinfection strategy. These and other proposed antiviral methodologies are ultimately limited by their toxicity to human cells. As a practical solution, surfaces that are safe for human contact and capable of spontaneously inactivating viruses are desirable to control the spread of viral diseases.

It is with these observations in mind, among others, that various aspects of the present disclosure were conceived and developed.

SUMMARY

Provided herein are embodiments of a method for capturing and inactivating a SARS-CoV-2 virus by contacting the virus with an object comprising silicon nitride and/or aluminum nitride.

In some aspects, the object may comprise silicon nitride or aluminum nitride, wherein the silicon nitride or aluminum nitride successively binds (i.e. captures) and then inactivates the virus. For example, the silicon nitride or the aluminum nitride may be present on the surface of the object as a coating or may be incorporated into the object. In some examples, the silicon nitride is present at a concentration from about 1 wt. % to about 30 wt. %.

In some aspects, the object may contact the virus for at least one minute or for at least 30 minutes. For example, the virus may be at least 75% inactivated after contact with the object for at least 1 minute. In some aspects, the object may comprise paper, cardboard, polymers, fabric, plastic, ceramic, stainless steel, and/or metal. In some aspects, the object is a protective gown, a body cover, a head cover, a shoe cover, a face mask, a face shield, an eye protector, gloves, a surgical gown, a surgical drape, or a cubicle curtain. In some additional aspects, the object is a face mask filter, a respirator filter, an air filtration filter, or an air ventilation filter. In even more aspects, the object is a knob, a handle, a railing, a bed frame, a bed tray, a table, a chair, an equipment rack, or a cart. In some additional aspects, the object may be composition such as a slurry, suspension, gel, paint, or toothpaste.

Also provided herein are embodiments of an article of personal protective equipment (PPE) having antiviral and antimicrobial properties. In some aspects, the article comprises silicon nitride or aluminum nitride. The silicon nitride or the aluminum nitride may be incorporated into the article or may be coated onto the surface of the article. In some aspects, the silicon nitride or aluminum nitride may be present at a concentration of about 1 wt. % to about 30 wt. %. In some aspects, the article may be a body cover, a head cover, a shoe cover, a face mask, a face and eye protector, or gloves. In some examples, the article is operable to bind/capture and then inactivate the SARS-CoV-2 virus upon contact with the virus.

BRIEF DESCRIPTION OF THE DRAWINGS

FIGS. 1A-1D are graphical representations that show the inactivation of SARS-CoV-2 by nitride powders treated with 15 wt. % Cu, AlN, and $Si_3N_4$ powders in an aqueous medium at room temperature for 1- and 10-minutes in which the control virus was treated identically without addition of any powders. After centrifugation, supernatants were subjected to $TCID_{50}$ assay. The Reed-Muench method was used to determine the virus titers. $TCID_{50}/50$ μL (FIGS. 1A and 1B) and % reduction FIGS. 1C and 1D are shown for virus inactivation times of 1 minutes and 10 minutes, respectively. Statistics are given in the inset according to unpaired two-tailed Student's t-test (n=3).

In FIG. 2A and FIG. 2B, virus suspensions were exposed to Cu, AlN and $Si_3N_4$ powders for 1 minute, and viral RNA in supernatants and on particles were evaluated using viral N gene "set 1" and "set 2" primers, respectively. Data collected on supernatants and pellet samples are given in comparison with the amount of viral N gene RNA in suspension that was left untreated. In FIG. 2C and FIG. 2D, results of RT-PCR tests after 10-minute exposure of supernatants to Cu, AlN and $Si_3N_4$ powders for viral N gene "set 1" and "set 2" primers are shown, respectively. Statistics are given in the inset according to unpaired two-tailed Student's t-test (n=3).

In FIG. 3E, non-inoculated cells (labeled as "sham-infected" cells) were also prepared and imaged for comparison. After fixation, cells were stained with anti-SARS coronavirus envelope antibody (red), Phalloidin to visualize F-actin (green), and DAPI to stain nuclei (blue). Fluorescence micrographs are shown, which are representative of n=3 samples.

in FIG. 5E, Raman spectrum of cells infected by unexposed virions (negative control). In FIG. 5F, a plot of the average intensity of the two tryptophan T1 and T2 bands (at 756 and 875 cm-1, respectively) as a function of fraction of infected cells by virions unexposed and exposed for 10-min to different particles (cf. labels); in the inset, the structure of N'-formylkynurenine, an intermediate in the catabolism of tryptophan upon enzymatic IDO reaction. In FIG. 5G, a graphical representation shows three possible conformations of tyrosine-based peptides that can justify the disappearance of ring vibrations in tyrosine (Ty2 band) upon chelation of Cu(II) ions.

Corresponding reference characters indicate elements among the view of the drawings. The headings used in the figures do not limit the scope of the claims.

DETAILED DESCRIPTION

Figure 2A:
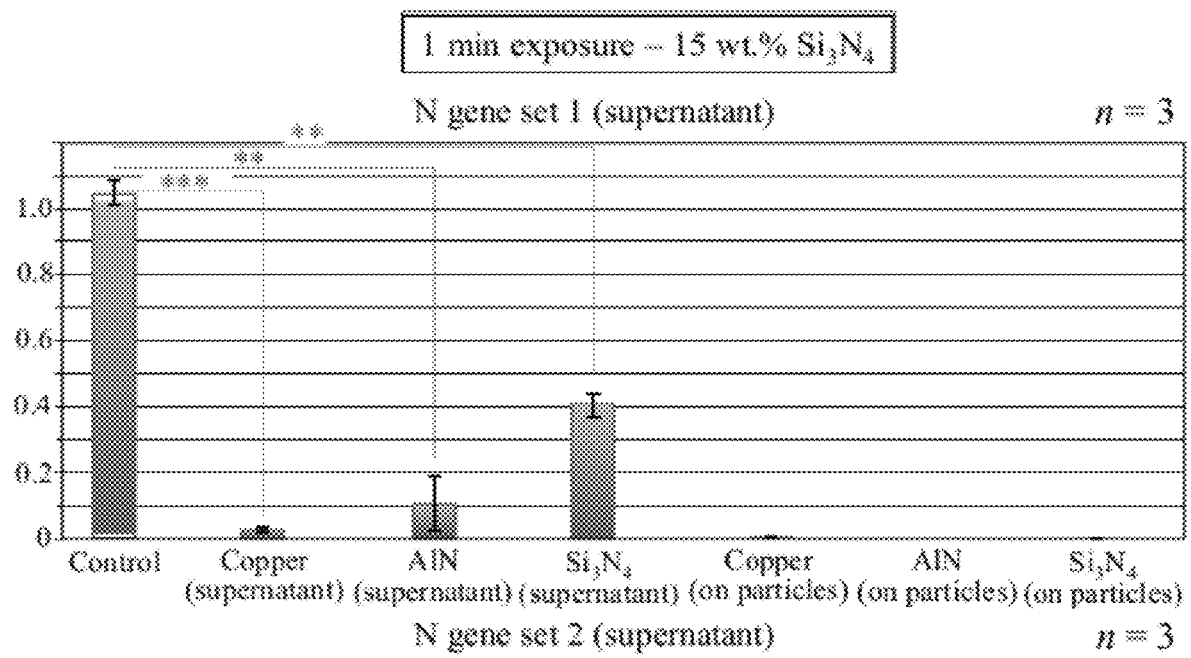
FIGS. 2A-2D are graphical representations that show viral RNA that has underwent severe degradation after exposure to copper or nitride particles.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description.

Several definitions that apply throughout this disclosure will now be presented. Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof."

As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

As used herein, the term "silicon nitride" includes α-$Si_3N_4$, β-$Si_3N_4$, SiYAlON, β-SiYAlON, SiYON, SiAlON, or combinations thereof.

As used herein, "inactivate" or "inactivation" refers to viral inactivation in which the virus is stopped from contaminating the product or subject either by removing virus completely or rendering them non-infectious.

The terms "object", "apparatus" or "component" as used herein include materials, compositions, devices, surface coatings, and/or composites. In some examples the apparatus may include various medical devices or equipment, examination tables, clothing, filters, personal protective equipment such as masks and gloves, catheters, endoscopic instruments, commonly-touched surfaces where viral persistence may encourage the spread of disease, and the like. The apparatus may be metallic, polymeric, and/or ceramic (ex. silicon nitride and/or other ceramic materials).

As used herein, "contact" means in physical contact or within close enough proximity to a composition or apparatus to be affected by the composition or apparatus.

As used herein, "personal protective equipment" or "PPE" means any device, article, or apparatus worn or otherwise used by a person to minimize exposure to pathogens or other harmful substances. Non-limiting examples of PPE include body covers, head covers, shoe covers, face masks, eye protectors, face and eye protectors, and gloves.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Provided herein is a method for inactivating the SARS-CoV-2 virus by contacting the virus with an object or composition comprising silicon nitride and/or aluminum nitride. The silicon nitride and/or aluminum nitride successively binds (i.e. captures) and then inactivates the virus (e.g. "catch and kill").

Silicon nitride possesses a unique surface chemistry which is biocompatible and provides a number of biomedical applications including 1) concurrent osteogenesis, osteoinduction, osteoconduction, and bacteriostasis, such as in spinal and dental implants; 2) killing of both gram-positive and gram-negative bacteria according to different mechanisms; 3) inactivation of human and animal viruses, bacteria, and fungi; and 4) polymer- or metal-matrix composites, natural or manmade fibers, polymers, or metals containing silicon nitride powder retain key silicon nitride bone restorative, bacteriostatic, antiviral, and antifungal properties.

Silicon nitride ($Si_3N_4$) is a non-oxide ceramic compound that has been used in many industries since the 1950s. A formulation of $Si_3N_4$ is FDA-cleared for use as an intervertebral spinal spacer in cervical and lumbar spine fusion surgery, with proven long-term safety, efficacy, and biocompatibility. Clinical data for $Si_3N_4$ implants compare favorably with other spine biomaterials, such as allograft, titanium, and polyetheretherketone. A curious finding is that $Si_3N_4$ implants have a lower incidence of bacterial infection (i.e., less than 0.006%) when compared to other implant materials (2.7% to 18%). This property reflects the complex surface biochemistry of $Si_3N_4$ that elutes minute amounts of nitrogen, which is converted to ammonia, ammonium, and other reactive nitrogen species (RNS) that inhibit bacteria. A recent investigation also found that viral exposure to sintered $Si_3N_4$ powders in aqueous suspension neutralized H1N1 (Influenza A/Puerto Rico/8/1934), Feline calicivirus, and Enterovirus (EV-A71). Based on these findings, $Si_3N_4$ may be able to inactivate SARS-CoV-2.

Silicon nitride may be antipathogenic due to release of nitrogen containing species when in contact with an aqueous medium, or biologic fluids and tissues. The surface chemistry of silicon nitride may be shown as follows:

$$Si_3N_4 + 6H_2O \rightarrow 3SiO_2 + 4NH_3$$

$$SiO_2 + 2H_2O \rightarrow Si(OH)_4$$

Nitrogen elutes faster (within minutes) than silicon because surface silanols are relatively stable. For viruses, it was surprisingly found that silicon nitride may provide for RNA cleavage via alkaline transesterification which leads to loss in genome integrity and virus inactivation. This may also reduce the activity of hemagglutinin. The elution of ammonia, along with an attendant increase in pH, inactivates viruses, bacteria, and fungi. As shown in the examples, it was surprisingly found that each of silicon nitride and aluminum nitride inactivates SARS-CoV-2.

The use of copper (Cu), a historically-recognized viricidal agent, is limited by its cell toxicity. In contrast to Cu, ceramic devices or apparatuses made of $Si_3N_4$ are biocompatible and not toxic to the human body. An advantage of $Si_3N_4$ is the versatility of the material; thus $Si_3N_4$ may be incorporated into polymers, bioactive glasses, and even other ceramics to create composites and coatings that retain the favorable biocompatible and antiviral properties of $Si_3N_4$.

The present disclosure compares the effects of exposing SARS-CoV-2 to aqueous suspensions of $Si_3N_4$ and aluminum nitride (AlN) particles and two controls, (i.e., a suspension of copper (Cu) particles (positive control) and a sham suspension of SARS-CoV-2 virions without any antiviral agent (negative control)). Copper (Cu) was chosen as a positive control because of its well-known ability to inactivate a variety of microbes, including viruses. Aluminum nitride was included in the testing because, like $Si_3N_4$, it is a nitrogen-based compound whose surface hydrolysis in aqueous solution leads to the elution of nitrogen, with an attendant increase in pH. Since comparable antiviral and antibacterial phenomena are believed to be operative for all nitride-based compounds, AlN was used to provide additional insight into the antipathogenic mechanisms of nitrogen-containing inorganic materials.

The persistence of human coronaviruses on common materials (e.g., metal, plastic, paper, and fabric) and touch surfaces (e.g., knobs, handles, railings, tables, and desktops) can contribute to the nosocomial and social spread of disease. Warnes et al. reported that at room temperature with 30%-40% humidity, the pathogenic human coronavirus 229E (HuCoV-229E) remained infectious in a lung cell model after at least 5 days of persistent viability on a variety of materials, such as Teflon, polyvinyl chloride, ceramic tile, glass, stainless steel, and silicone rubber. These investigators also showed rapid HuCoV-229E inactivation (within a few minutes) for simulated fingertip contamination on Cu surfaces. Cu ion release and the generation of reactive oxygen species (ROS) were involved in viral inactivation; and increased contact time with copper and brass surfaces led to greater non-specific fragmentation of viral RNA, indicating irreversible viral inactivation. More recently, Doremalen et al. showed surface stability of both SARS-CoV-1 and SARS-CoV-2 virus on plastic, cardboard, stainless steel, and even Cu surfaces for 4-72 hours after application. While breathable N95-rated masks can capture particulates before they can be inhaled, SARS-CoV-2 virus particles remain active in mask filters for up to 7 days. Contact killing of viruses, such as observed on Cu surfaces is, therefore, receiving renewed interest as a disease mitigation strategy.

Surprisingly, compounds capable of endogenous nitrogen-release, such as $Si_3N_4$ and AlN, can inactivate the SARS-CoV-2 virus at least as effectively as Cu. Without being limited to any one theory, multiple antiviral mechanisms may be operative, such as RNA fragmentation, and in the case of Cu and AlN, direct metal ion toxicity; but while Cu and AlN supernatants demonstrated cellular lysis, $Si_3N_4$ may provoke no metabolic alterations. The Raman spectrum of VeroE6 cells exposed to the $Si_3N_4$ viral supernatant was like that of the uninfected sham. These findings indicate that while $Si_3N_4$, Cu, and AlN were all capable of inactivating the SARS-CoV-2 virus, $Si_3N_4$ was the safest.

The antiviral effect may be related to the electrical attraction (including "competitive binding" to an envelope glycoprotein hemagglutinin in the case of influenza virus) and viral RNA fragmentation by reactive nitrogen species (RNS). These phenomena are due to the slow and controlled elution of nitrogen from $Si_3N_4$'s surface which forms ammonia ($NH_3$) and ammonium ($NH_4^+$) moieties coupled with the release of free electrons and negatively charged silanols in aqueous solution.

Figure 6:
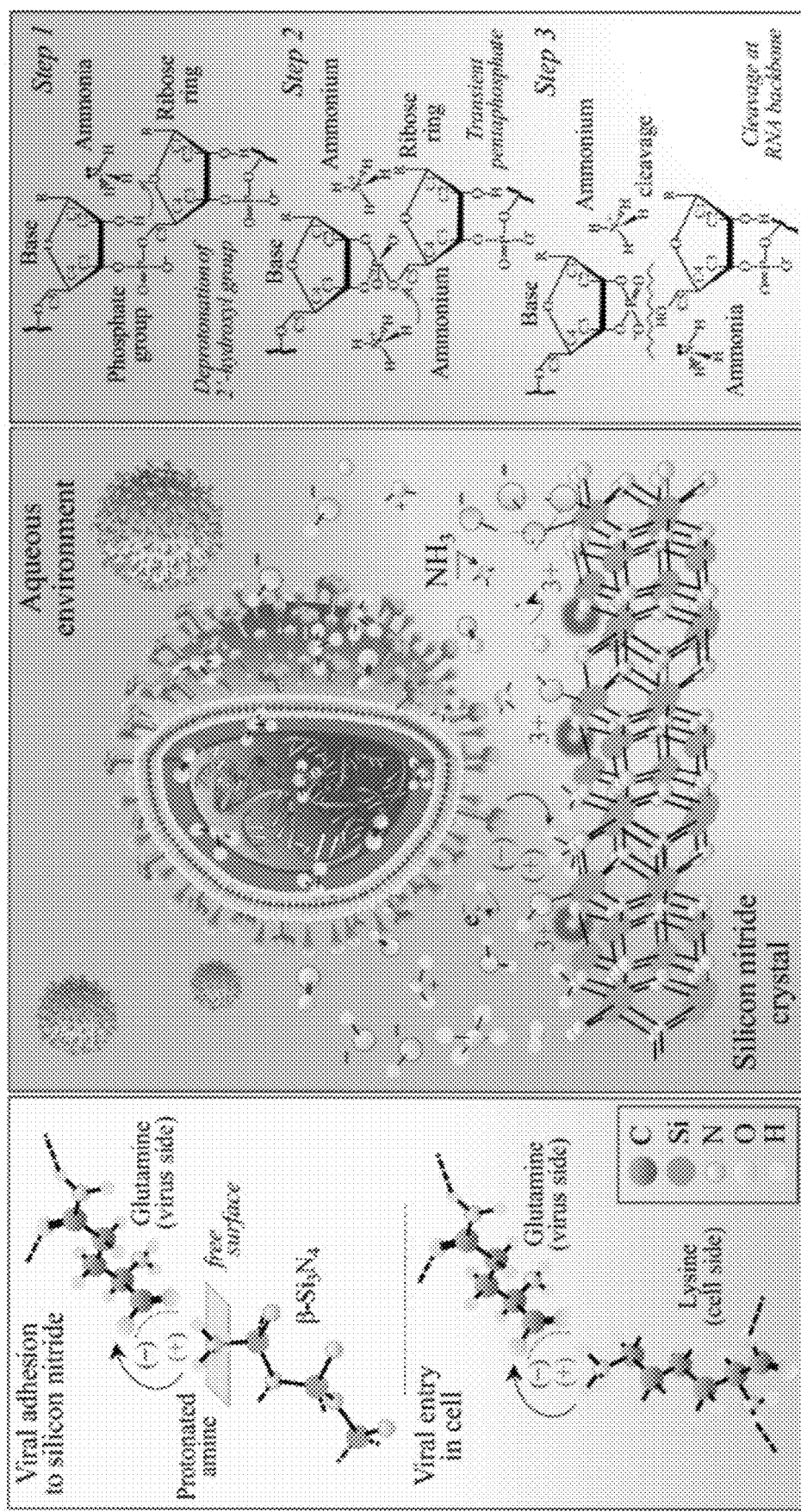
FIG. 6 is a schematic model illustrating a chemical and electrical charge similarity between the protonated amine groups, Si—$NH_3^+$, at the surface of $Si_3N_4$ and the N-terminal of lysine, C—$NH_3^+$ in cells (left panel); and, the interaction of SARS-CoV-2 viruses with the charged molecular species at the surface of $Si_3N_4$ (specifically, at protonated amines charging plus) and the eluted species $NH_3/NH_4^+$ (central panel). The eluted N leaves 3+ charged vacancies on the solid surface (violet-colored sites), which stem together with negatively charged silanols. The three-step process leading to RNA backbone cleavage by the eluted nitrogen species (namely, deprotonation of 2'-hydroxyl groups, formation of a transient pentaphosphate, and cleavage of the phosphodiester bond in the RNA backbone by alkaline transesterification through hydrolysis) is shown in the right panel. Note that the similarity between protonated amine and N-terminal of lysine might trigger an extremely effective "competitive binding" mechanism for SARS-CoV-2 virion inactivation, while eluted ammonia fatally degrades the virion RNA in a combined "catch and kill" effect.

In the context of SARS-CoV-2 viral inactivation, two important aspects of $Si_3N_4$'s surface chemistry play fundamental roles: (i) the similarity between the protonated amino groups, Si—$NH_3^+$ at the surface of $Si_3N_4$ and the N-terminal of lysine, C—$NH_3^+$ on the virus; and, (ii) the elution of gaseous ammonia due to $Si_3N_4$ hydrolysis. A schematic representation of the interaction between SARS-CoV-2 and the $Si_3N_4$ surface is given in FIG. 6 (central panel). The similarity is depicted in the left panel of this figure. It triggers an extremely effective "competitive binding" approach to SARS-CoV-2 inactivation which stems from several successful other examples such as Hepatitis B and Influenza A. The strong antiviral effect of eluted (gaseous) $NH_3$ is due to its penetration of the virions and its reaction with the RNA backbone. The RNA undergoes alkaline transesterification through the hydrolysis of its phosphodiester bonds. RNA phosphodiester bond cleavage is schematically depicted in the right panel of FIG. 6. The RT-PCR and fluorescence microscopy results of the present study suggest contributions from both mechanisms to the inactivation of SARS-CoV-2, consistent with earlier work. The $TCID_{50}$ results shown in FIGS. 1A-1D and the RT-PCR data of FIGS. 2A-2D for viral RNA harvested from either the supernatant or the $Si_3N_4$ particles provide important information about these mechanisms. Although >99% inactivation was achieved after exposure to $Si_3N_4$ for 1-min, (FIG. 1B), only partial viral RNA fragmentation was observed for the supernatant (FIG. 2A) while RNA harvested from the $Si_3N_4$ particles (FIG. 2B) was essentially fully fragmented. Note that the opposite effect was found for Cu. This suggests that the mechanism of inactivation for $Si_3N_4$, as depicted in the left panel of FIG. 6, had successive events of "competitive binding" and ammonia poisoning—a kind of "catch and kill" scenario. The complete RNA fragmentation at 10-minute exposure to $Si_3N_4$ suggests that nitrogen elution is a key process that triggers a cascade of reactions which result in virus inactivation (cf. right panel in FIG. 6)

In some embodiments, an object, article, or composition comprising silicon nitride or aluminum nitride may be operable to successively bind a virus (e.g. SARS-Cov-2) and then inactivate the virus.

The antiviral effectiveness of $Si_3N_4$ may be comparable to Cu. While Cu is an essential trace element for human health and an electron donor/acceptor for several key enzymes by altering redox states between $Cu^+$ and $Cu^{2+}$, these properties can also cause cellular damage. Its use as an antiviral agent is limited by allergic dermatitis, hypersensitivity, and multi-organ dysfunction. In contrast, the safety of $Si_3N_4$ as a permanently-implanted material during spine fusion surgery is well established by experimental and clinical data. Therefore, an object, article, or composition comprising silicon nitride may be as effective at inactivating a virus as Cu without the negative effects of Cu.

$Si_3N_4$ is well-known for its capabilities as an industrial material. Load-bearing $Si_3N_4$ prosthetic hip bearings and spinal fusion implants were initially developed because of the superior strength and toughness of $Si_3N_4$. Later studies showed other properties of $Si_3N_4$ that are favored in designing orthopaedic implants, such as enhanced osteoconductivity, bacteriostasis, improved radiolucency, lack of implant subsidence, and wear resistance. Therefore, $Si_3N_4$'s surface chemistry, topography, and hydrophilicity contribute to a dual effect (i.e., upregulation of osteogenic activity to promote spinal fusion while simultaneously preventing bacterial adhesion and biofilm formation). In addition to its proven record as a bioimplant, an advantage of $Si_3N_4$ is its versatility of manufacture. Sintered powders of $Si_3N_4$ have been incorporated into other materials, such as polymers, other ceramics, bioglass, and metals, to create composite structures that maintain the index osteogenic and antibacterial properties of monolithic $Si_3N_4$. Three-dimensional additive deposition of $Si_3N_4$ may enable the manufacture of protective surfaces in health care that reduce fomite-mediated transmission of microbial disease. Incorporation of $Si_3N_4$ particles into the fabric of personal protective equipment, such as face masks, protective gowns, and surgical drapes could contribute to health workers as well as patient safety.

$Si_3N_4$ inactivates the SARS-CoV-2 virus in a matter of minutes following exposure. Without being limited to any one theory, the mechanism of action may be shared with other nitrogen-based compounds that express trace amounts of surface disinfectants, such as aluminum nitride.

In some embodiments, the object used to bind and inactivate the SARS-CoV-2 virus is a device or apparatus that may include a silicon nitride and/or aluminum nitride composition on at least a portion of a surface of the object. The silicon nitride or aluminum nitride coating may be applied to the surface of the object as a powder. In some examples, the silicon nitride or aluminum nitride powder may be filled, embedded, or impregnated in at least a portion of the object. In some embodiments, the powder may have particles in the micron, submicron or nanometer size range. The average particle size may range from about 100 nm to about 5 μm, from about 300 nm to about 1.5 μm, or from about 0.6 μm to about 1.0 μm. In other embodiments, the silicon nitride or aluminum nitride may be incorporated into the device. For example, an object may incorporate a silicon nitride and/or aluminum nitride powder within the body of the object. In one embodiment, the device may be made of silicon nitride. In another embodiment, the object may be made of aluminum nitride. In yet another embodiment, the object can comprise a slurry or suspension of aluminum nitride or silicon nitride particles.

In some embodiments, the object may further comprise other materials including, but not limited to, paper, cardboard, fabric, plastic, ceramic, polymers, stainless steel, metal, or a combination thereof. Some non-limiting examples of the object may include surgical gowns, surgical drapes, shoe covers, cubicle curtains, tubing, clothing, gloves, eye protectors, masks including surgical masks and face shields, PPE, tables such as hospital exam and surgical tables, chairs, bed frames, bed trays, desks, fixtures, cabinets, equipment racks, carts, handles, knobs, railings, toys, water filters, and air filters such as face mask filters, respirator filters, air filtration filters, and air ventilation filters, or air conditioner filters. In some examples, the filters may be within filtration devices of anesthesia machines, ventilators, or CPAP machines such that an antimicrobial surface layer in the filter can trap pulmonary pathogens, as air moves in and out of infected lungs. In various embodiments, the object may be a medical device or apparatus. Non-limiting examples of medical devices or apparatuses include orthopedic implants, spinal implants, pedicle screws, dental implants, in-dwelling catheters, endotracheal tubes, colonoscopy scopes, and other similar devices.

In other embodiments, the object may be a composition incorporating silicon nitride or aluminum nitride powder therein including, but not limited to slurries, suspensions, gels, sprays, paint, or toothpaste. For example, the addition of silicon nitride or aluminum nitride to a slurry, such as paint, that is then applied to a surface may provide an antibacterial, antifungal, and antiviral surface. In other embodiments, silicon nitride or aluminum nitride may be mixed with water along with any appropriate dispersants and slurry stabilization agents, and thereafter applied by spraying the slurry onto various surfaces. An example dispersant is Dolapix A88.

The silicon nitride or aluminum nitride coating may be present on the surface of the object in a concentration of about 1 wt. % to about 100 wt. %. The silicon nitride and/or aluminum nitride may be coated onto or layered into the object. In various embodiments, the coating may include about 1 wt. %, 2 wt. %, 5 wt. %, 7.5 wt. %, 8.3 wt. %, 10 wt. %, 15 wt. %, 16.7 wt. %, 20 wt. %, 25 wt. %, or about 30 wt. % silicon nitride powder or aluminum nitride powder. In some examples, the coating may include about 10 wt. % to about 20 wt. % silicon nitride or aluminum nitride. In at least one example, the coating includes about 15 wt. % silicon nitride or aluminum nitride. In some embodiments, silicon nitride or aluminum nitride may be embedded in (as a filler) or on the surface of the object in a concentration of about 1 wt. % to about 100 wt. %. In various embodiments, the object may include about 1 wt. %, 2 wt. %, 5 wt. %, 7.5 wt. %, 8.3 wt. %, 10 wt. %, 15 wt. %, 16.7 wt. %, 20 wt. %, 25 wt. %, 30 wt. %, 33.3 wt. %, 35 wt. %, 40 wt. %, 50 wt. %, 60 wt. %, 70 wt. %, 80 wt. %, 90 wt. %, to 100 wt. % silicon nitride or aluminum nitride. In some examples, the silicon nitride or aluminum nitride may be on the surface of the object at a concentration of about 10 wt. % to about 20 wt. %. In at least one example, the silicon nitride or aluminum nitride may be on the surface of the object at a concentration of about 15 wt. %. In some aspects, the concentration of silicon nitride or aluminum nitride may depend on the substrate material of the object, such as paper, cardboard, fabric, plastic, ceramic, polymers, stainless steel, and/or metal. In some embodiments, the substrate material of the object may be a polymer and the polymer may have a practical limit (i.e. percolation limit) on the amount of silicon nitride and/or aluminum nitride that may be incorporated into the object.

In some embodiments, the object may be a monolithic component consisting of the silicon nitride or aluminum nitride. Such an object may be fully dense possessing no internal porosity, or it may be porous, having a porosity that ranges from about 1% to about 80%. The monolithic object may be used as a medical device or may be used in an apparatus in which the inactivation of a virus may be desired.

In some embodiments, the object may contact the SARS-CoV-2 virus for a limited period of time. The object may be in contact with the SARS-CoV-2 virus for about 1 min to about 2 hours in order to inactivate the virus. In various examples, the object may contact the SARS-CoV-2 virus for at least 30 seconds, at least 1 minute, at least 5 minutes, at least 30 minutes, at least 1 hour, at least 2 hours, at least 5 hours, or at least 1 day. In at least one example, the object may be permanently implanted in the patient. In at least one example, the object may be worn externally by a user. In another example, the object may be permanently implanted in the patient. In yet another example, the object may be a high contact surface. In further examples, the object may be in continuous or sustained contact with a body fluid of a patient. The body fluid may be blood or gas (e.g., inhalation or exhalation gas).

In some embodiments, the virus is at least 70% inactivated, at least 75% inactivated, at least 80% inactivated, at least 85% inactivated, at least 90% inactivated, at least 95% inactivated, or at least 99% inactivated after contact with the object for at least 1 minute, at least 5 minutes, or at least 30 minutes. In at least one example, the virus is at least 85% inactivated after contact with object for at least 1 minute. In another example, the virus is at least 99% inactivated after contact with the object for at least 30 minutes. In yet another example, the virus is at least 99% inactivated after contact with the object for at least 1 minute.

Also presented herein is an article of personal protective equipment having antiviral and antimicrobial properties. The article may comprise silicon nitride or aluminum nitride incorporated into the article or the silicon nitride or aluminum nitride may be coated onto the surface of the article.

The silicon nitride or aluminum nitride coating may be present on the surface of the article in a concentration of about 1 wt. % to about 100 wt. %. In various embodiments, the coating may include about 1 wt. %, 2 wt. %, 5 wt. %, 7.5 wt. %, 8.3 wt. %, 10 wt. %, 15 wt. %, 16.7 wt. %, 20 wt. %, 25 wt. %, or about 30 wt. % silicon nitride powder or aluminum nitride powder. In some examples, the coating may include about 10 wt. % to about 20 wt. % silicon nitride or aluminum nitride. In at least one example, the coating includes about 15 wt. % silicon nitride or aluminum nitride. In some embodiments, silicon nitride or aluminum nitride may be embedded in (as a filler) or on the surface of the article in a concentration of about 1 wt. % to about 100 wt. %. In various embodiments, the object may include about 1 wt. %, 2 wt. %, 5 wt. %, 7.5 wt. %, 8.3 wt. %, 10 wt. %, 15 wt. %, 16.7 wt. %, 20 wt. %, 25 wt. %, 30 wt. %, 33.3 wt. %, 35 wt. %, 40 wt. %, 50 wt. %, 60 wt. %, 70 wt. %, 80 wt. %, 90 wt. %, to 100 wt. % silicon nitride or aluminum nitride. In some examples, the silicon nitride or aluminum nitride may be on the surface of the article at a concentration of about 10 wt. % to about 20 wt. %. In at least one example, the silicon nitride or aluminum nitride may be on the surface of the article at a concentration of about 15 wt. %. In some aspects, the concentration of silicon nitride or aluminum nitride may depend on the substrate material of the object.

In some embodiments, the article is PPE. In some aspects, the article is a body cover, a head cover, a shoe cover, a face mask, a face and eye protector, or gloves. In some aspects, the article is operable to inactivate a SARS-CoV-2 virus when the article contacts the virus.

EXAMPLES

Example 1

Preparation of Test Materials $Si_3N_4$, Cu, and AlN powders were acquired from commercial sources. $Si_3N_4$ powder (nominal composition of 90 wt. % $Si_3N_4$, 6 wt. % $Y_2O_3$, and 4 wt. % $Al_2O_3$) was prepared by aqueous mixing and spray-drying of the inorganic constituents, followed by sintering of the spray-dried granules (1700° C. for ~3 h), hot-isostatic pressing (1600° C., 2 h, 140 MPa in $N_2$), aqueous-based comminution, and freeze-drying. The resulting powder had an average particle size of 0.8±1.0 μm. As-received Cu powder (USP grade 99.5% purity) granules were comminuted to achieve a particle size comparable to the $Si_3N_4$. AlN powder had an average particle size of 1.2±0.6 μm as-received, which was comparable to $Si_3N_4$.

Preparation of Mammalian and Viral Cells

VeroE6/TMPRSS2 mammalian cells were used in the viral assays. Cells were grown in Dulbecco's modified Eagle's minimum essential medium (DMEM) supplemented with G418 disulfate (1 mg/ml), penicillin (100 units/mL), streptomycin (100 μg/mL), 5% fetal bovine serum, and maintained at 37° C. in a 5% CO2/95% in a humidified atmosphere. The SARS-CoV-2 viral stock was propagated using VeroE6/TMPRSS2 cells at 37° C. for 2 days. Viral titers were assayed by a median tissue culture infectious dose ($TCID_{50}$).

Example 2

Virus Assays

Fifteen weight percent (15 wt. %) of the $Si_3N_4$, Cu, and AlN powders were separately dispersed in 1 mL of PBS(–), followed by the addition of the viral suspension ($2\times10^5$ $TCID_{50}$ in 20 µL). Due to the higher density of the Cu powder, its volumetric fraction was approximately one-third of the $Si_3N_4$. Mixing was performed for 1 and 10 minutes by slow manual rotation at 4° C. After exposure, the powders were pelleted by centrifugation (2400 rpm 2 minutes) followed by filtration through a 0.1 µm media. Supernatants were collected and subjected to $TCID_{50}$ assays, real-time RT-PCR testing, and fluorescence imaging. Experiments were performed in triplicate including sham supernatants without the antiviral powders. A confluent monolayer of VeroE6/TMPRSS2 cells in a 96-well plate was inoculated with 50 µL/well of each virus suspension in a tenfold serial dilution with 0.5% FBS DMEM (i.e., maintenance medium). Viral adsorption at 37° C. for 1 hour was made with tilting every 10 minutes. Afterwards, 50 µL/well of the maintenance medium was added. The plate was incubated at 37° C. in a 5% CO2/95% humidified atmosphere for 4 days. The cytopathic effect (CPE) of the infected cells was observed under a phase-contrast microscope. The cells were subsequently fixed by adding 10 µL/well of glutaraldehyde followed by staining with 0.5% crystal violet. The $TCID_{50}$ was calculated according to the Reed-Muench method.

Viral RNA Assay

After exposure to the powders, 140 µL of the supernatants were used for viral RNA extraction. RNA was also extracted from the surfaces of the centrifuged and filtered powders. RNA purification was performed by using a QIAamp Viral RNA Mini kit. An aliquot of 16 µL of isolated RNA was reverse-transcribed using ReverTra Ace® qPCR RT Master Mix. Quantitative real-time PCR was performed using a Step-One Plus Real-Time PCR system primers/probes for two specific viral N gene sets. Each 20 µL reaction mixture contained 4 µL of cDNA, 8.8 µmol of each primer, 2.4 µmol of the probe, and 10 µL GoTaq Probe qPCR master mix. The amplification protocol consisted of 50 cycles of denaturation at 95° C. for 3 seconds and annealing and extension at 60° C. for 20 seconds.

Immunochemical Fluorescence Assay

Vero E6/TMPRSS2 cells on cover glass were inoculated with 200 µL of virus supernatant. After viral adsorption at 37° C. for 1 hour, the cells were incubated with the maintenance medium in a CO2 incubator for 7 hour. For the detection of infected cells, these cells were washed with TBS (20 mM Tris-HCl pH 7.5, 150 mM NaCl) and fixed with 4% PFA for 10 min at room temperature (RT) followed by membrane permeabilization with 0.1% Triton X in TBS for 5 minutes at RT. The cells were blocked with 2% skim milk in TBS for 60 minutes at RT and stained with anti-SARS Coronavirus envelope (Rabbit) antibody (Dilution=1: 100) for 60 minutes at RT. After washing with a buffer, cells were incubated with an Alexa 594 Goat Anti-Rabbit IgG (H+L) (1:500) and Alexa 488 Phalloidin (1:50) for 60 min at RT in the dark. ProLong™ Diamond Antifade Mountant with DAPI was used as a mounting medium. The staining was observed under a fluorescent microscope BZX710. The total cell and infected cell counts were obtained using the Keyence BZX Analyzer.

Raman Spectroscopy Assay

Vero E6/TMPRSS2 cells were infected with 200 µL of each virus suspension onto glass sites. After viral adsorption at 37° C. for 1 hours, the infected cells were incubated with the maintenance medium in a $CO_2$ incubator for 4 hours and fixed with 4% paraformaldehyde for 10 minutes at RT. After washing with distilled water twice, infected cells were air-dried and in situ analyzed using a Raman microprobe spectrometer. Raman spectra were collected using a highly sensitive spectroscope with a 20× optical lens. It operated in microscopic measurement mode with confocal imaging in two dimensions. A holographic notch filter within the optical circuit was used to efficiently achieve a spectral resolution of 1.5 cm-1 via a 532 nm excitation source operating at 10 mW. Raman emissions were monitored using a single monochromator connected to an air-cooled charge-coupled device (CCD) detector 1024×256 pixels). The acquisition time was fixed at 10 seconds. Thirty spectra were collected and averaged for each analysis time-point. Raman spectra were deconvoluted into Gaussian-Lorentzian sub-bands using commercially available software.

Statistical Analysis

The Student's t-test determined statistical significance for n=3 and at a p-value of 0.01 using Prism software.

Example 3

Median Tissue Culture Infection Dose $TCID_{50}$ assay results for the 15 wt. % $Si_3N_4$, Cu, and AlN powders are shown in FIGS. 1A-1D. Inactivation times of 1 and 10 minutes are shown in FIGS. 1A and 1B as well as FIGS. 1C and 1D, respectively. Relative to the negative control, all three powders were effective in inactivating SARS-CoV-2 virions (>99%) for the two exposure times.

RNA Gene Fragmentation

Figure 2B:
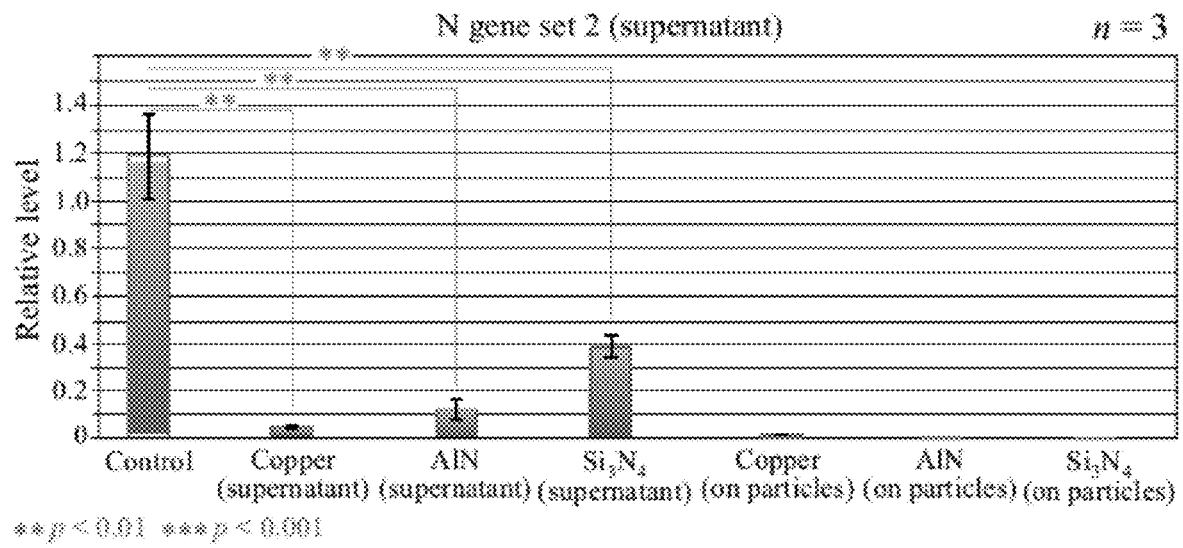
Figure 2C:
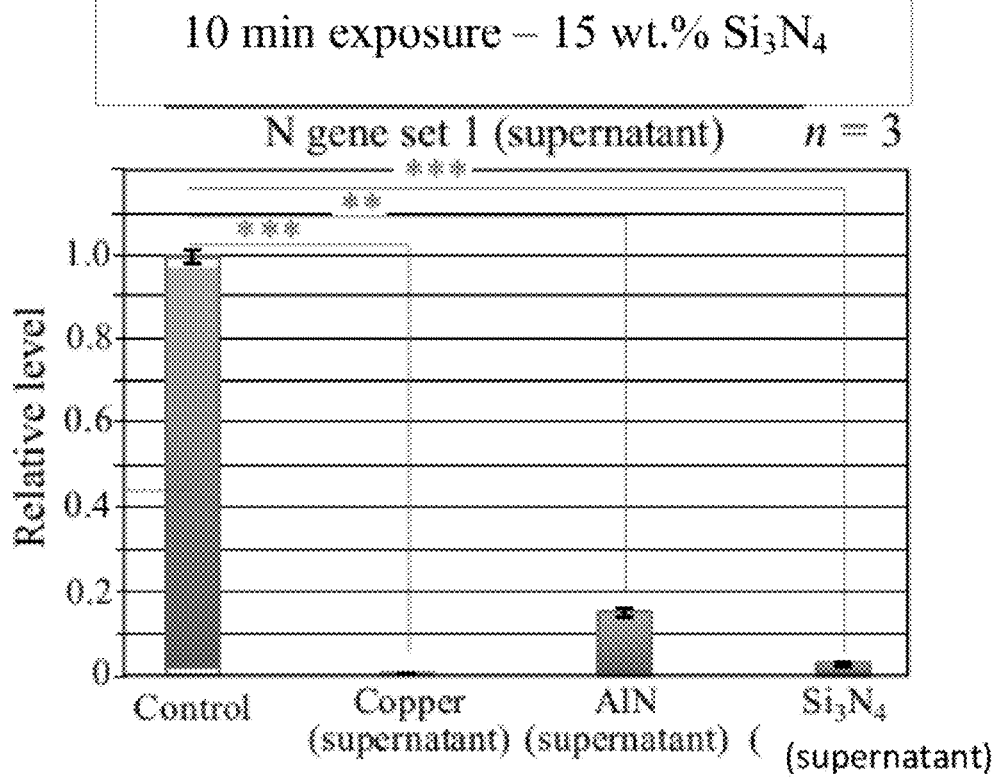
Figure 2D:
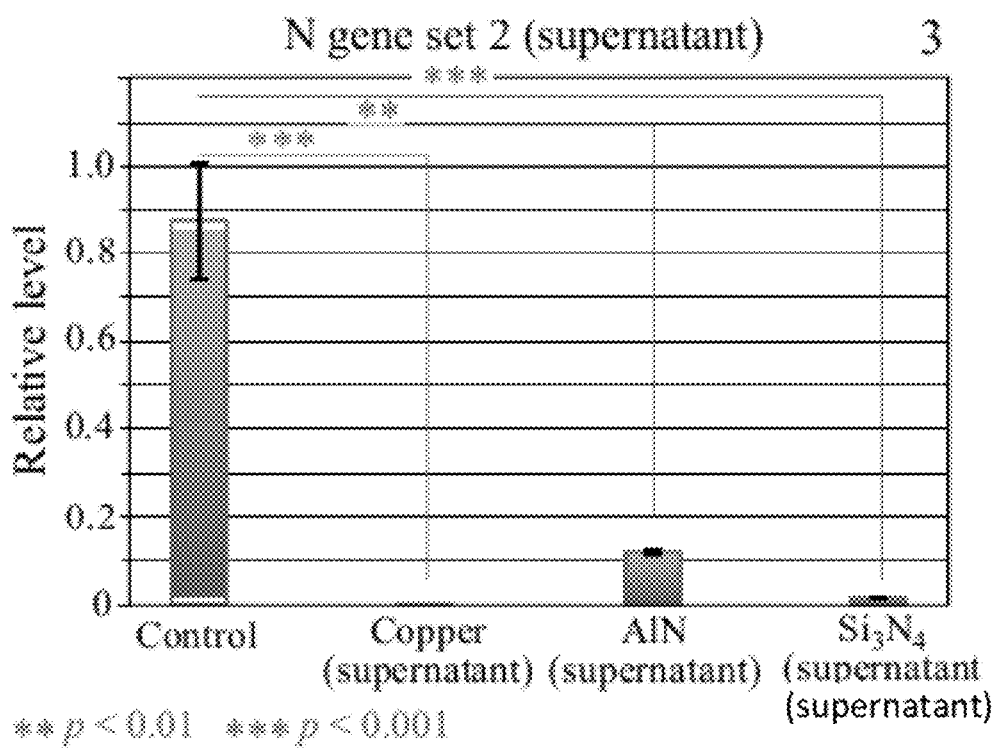

To examine whether viral RNA was fragmented from exposure to both the supernatants and powders, RT-PCR tests were conducted on the N gene sets of the virus' RNA. The results are shown in FIGS. 2A and 2B as well as FIGS. 2C and 2D for 1- and 10-minute exposures, respectively. Again, in comparison to the negative control at 1 minute of exposure to the supernatants, almost complete fragmentation of the RNA was observed for Cu while significant damage was caused by AlN and to a lesser extent by $Si_3N_4$. After 10-minute exposure to the supernatants, substantial cleavage of the RNA was seen for all three materials. While Cu still showed the most fragmentation, $Si_3N_4$ demonstrated similar effectiveness, and AlN was essentially identical to the 1-minute exposure condition. Viral RNA was virtually undetectable for all three materials based on extracted RNA from the pelleted powders at 1-minute of exposure (cf., FIGS. 2A and 2B). This result suggests that the decrease of viral RNA in the supernatant was not because of adherence of the RNA to the powders, but rather due to direct degradation.

Immunofluorescence Testing

Figure 3A:
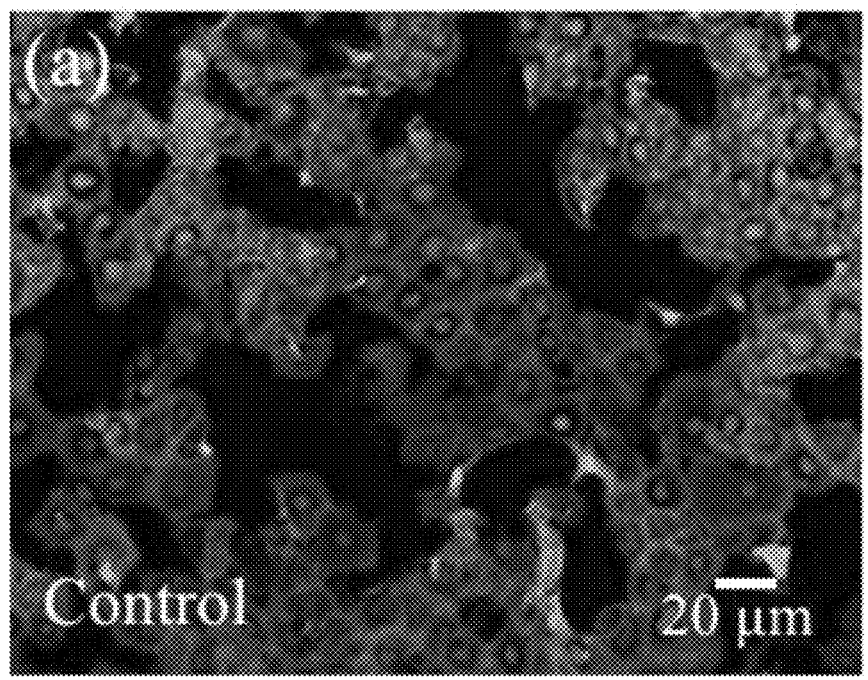
FIGS. 3A-3E are images showing $Si_3N_4$ suppressed virus infection without affecting cell viability in which Cu killed the cells. VeroE6/TMPRSS2 cells were inoculated with (FIG. 3A) unexposed virions, and virions 10-minute UTE-exposed to $Si_3N_4$ (FIG. 3B), AlN (FIG. 3C), and Cu (FIG. 3D).
Figure 3B:
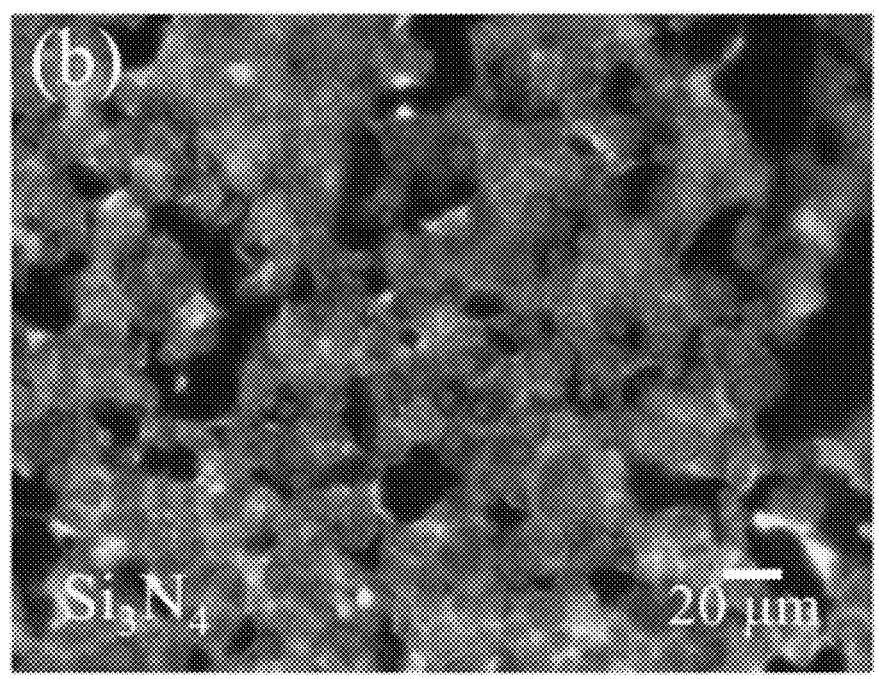
Figure 3C:
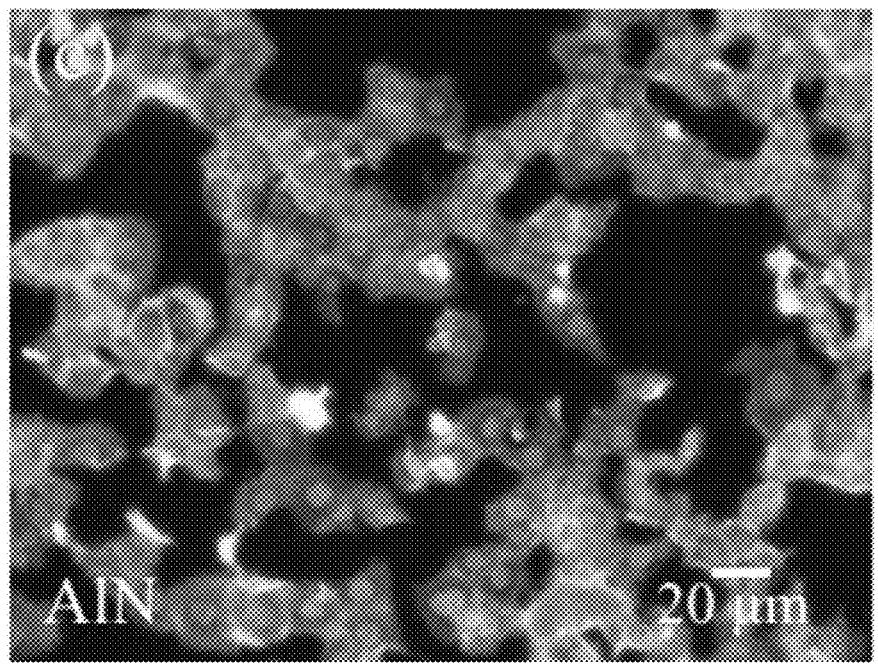
Figure 3D:
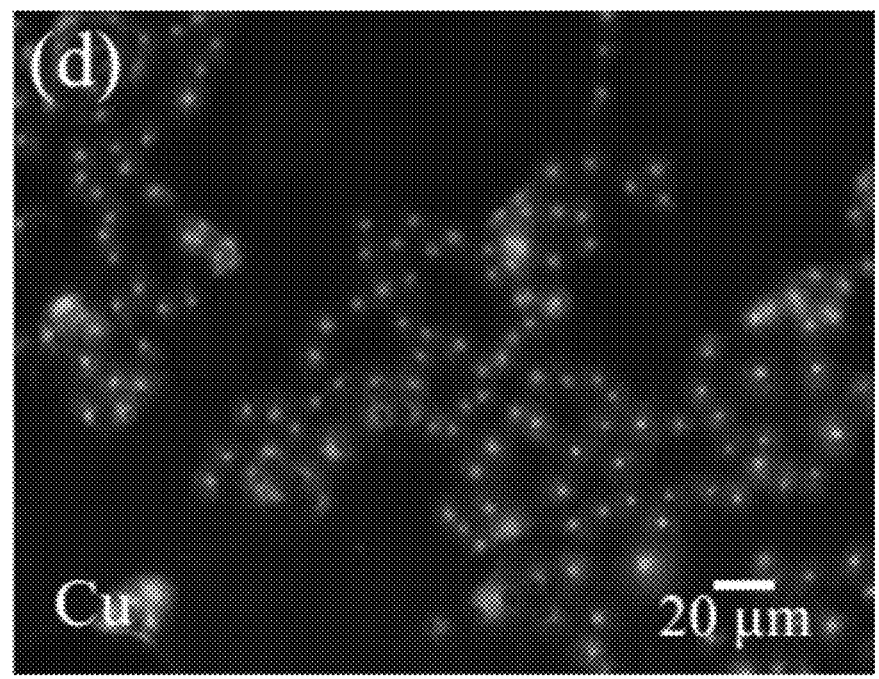
Figure 3E:
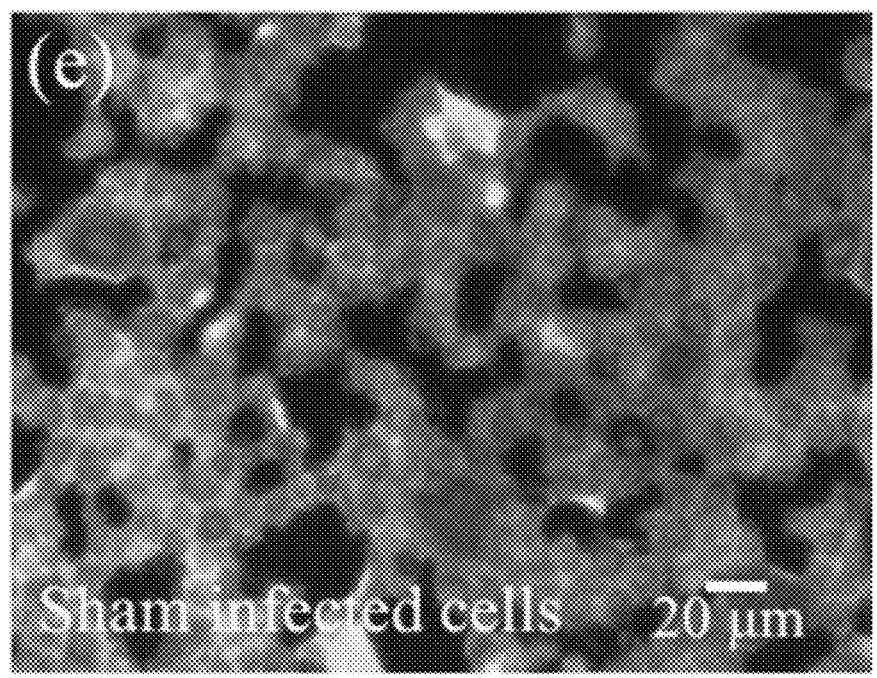

Immunofluorescence imaging using anti-SARS coronavirus envelope antibody (red), Phalloidin that stains F-actin in viable cells (green), and DAPI for cell nuclear staining (blue) was then used to confirm the $TCID_{50}$ assay and gene fragmentation results. FIGS. 3A-3D show fluorescence micrographs representative of the VeroE6/TMPRSS2 cell populations that were inoculated with supernatants of (a) unexposed virions (i.e., negative control) and 10-minute-exposed virions of (b) $Si_3N_4$, (c) AlN, and (d) Cu. FIG. 3E shows cells that were not inoculated with the virus (labeled as "sham-infected" cells. The red-colored spots in the negative control (FIG. 3A) demonstrated that the virions had entered and hijacked the Vero6E cells' metabolism. This contrasts with the sham-infected cells (FIG. 3E) which showed normal metabolic function.

Figure 4:
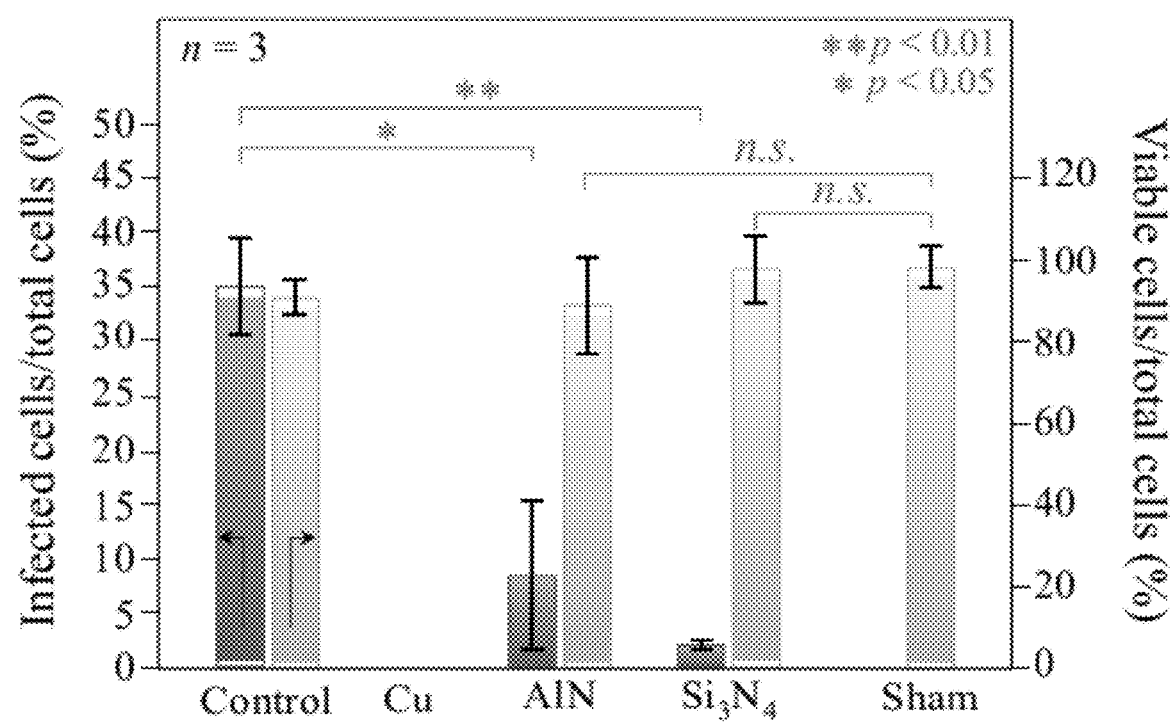
FIG. 4 is a graphical representation showing fluorescently labeled and non-labeled cells were counted on fluorescence micrographs, and % infected cells and % viable cells calculated as follows: % infected cells=(number of the cells stained with anti-SARS coronavirus envelope antibody)/(number of cells stained with DAPI)×100; and, % viable cells=(number of the cells stained with Phalloidin)/(number of cells stained with DAPI)×100. Data is representative of n=3 samples. * and ** are p<0.05 and 0.01, respectively, by unpaired two-tailed Student's t-test (n=3); n.s.=non-significant.

Remarkably, cells inoculated with supernatants from $Si_3N_4$ and, to a lesser extent, from AlN demonstrated near-normal function with few infections. Conversely, cells inoculated with the Cu supernatant were essentially dead (i.e., a complete lack of F-actin, FIG. 3D), although based on the bluish-red stains present in the nuclei, they may have been viable premortem because virions appear to have hijacked some nuclei. This suggests that cellular lysis was not only the result of the viral infection but also due to toxic effects from intracellular free Cu ions. Quantification of the colorimetric results from FIGS. 3A-3E is provided in FIG. 4. These data demonstrate that about 35% of the viable VeroE6 cells from the negative control were infected by virions, whereas only 2% and 8% of cells inoculated with supernatants from $Si_3N_4$ and AlN were infected, respectively. Quantitative evaluation of the cells inoculated with the Cu supernatant could not be assessed due to their premature death.

Raman Spectroscopy

Figure 5A:
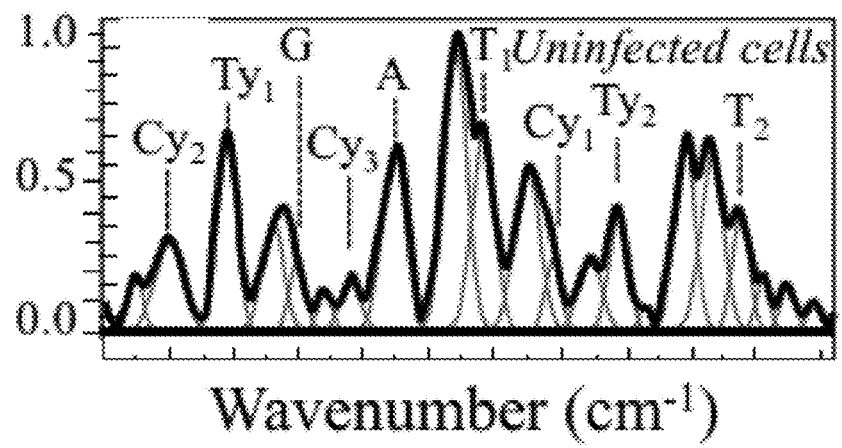
FIGS. 5A-5G are graphical representations of Raman spectra for: (a) uninfected cells (FIG. 5A) (i.e., unexposed to virions), and cells infected with SARS-CoV-2 virions exposed for 10 minutes to (b) $Si_3N_4$ (FIG. 5B), (c) AlN (FIG. 5C), and (d) Cu (FIG. 5D)
Figure 5B:
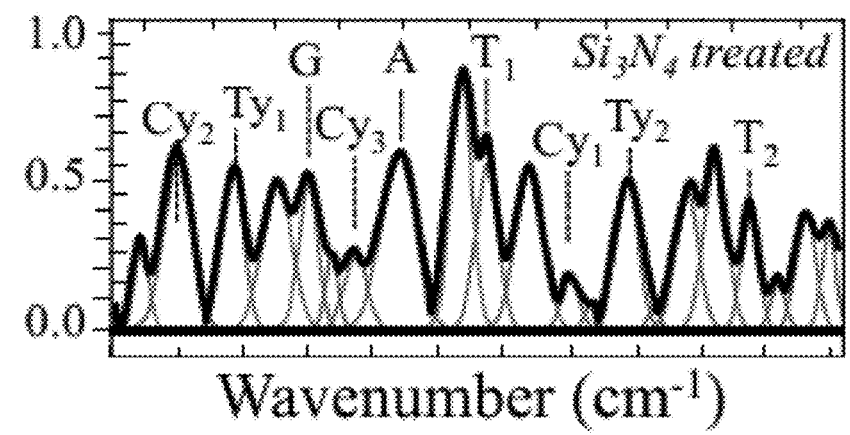
Figure 5C:
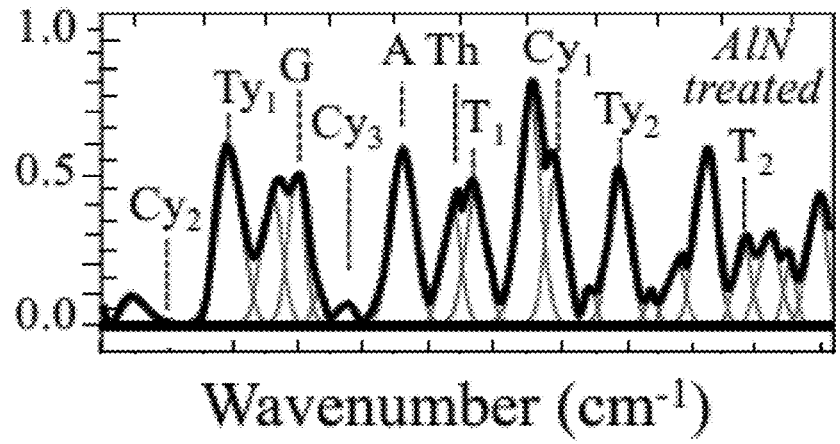
Figure 5D:
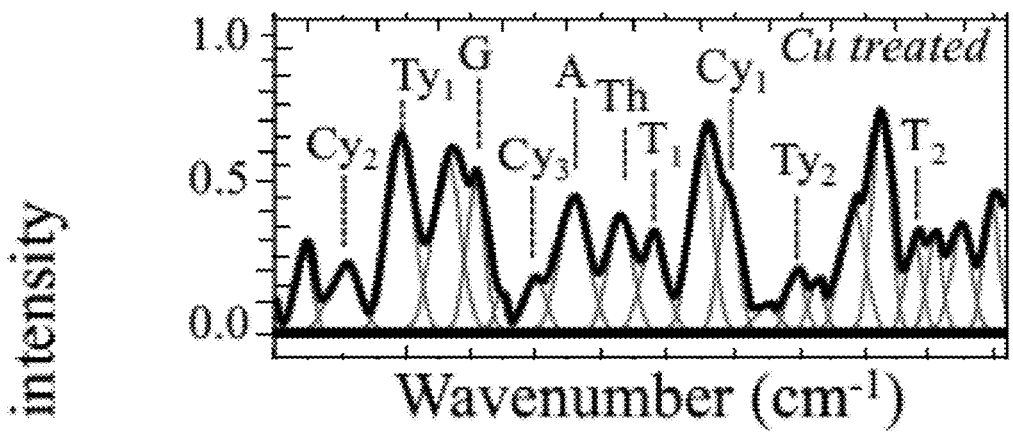
Figure 5E:
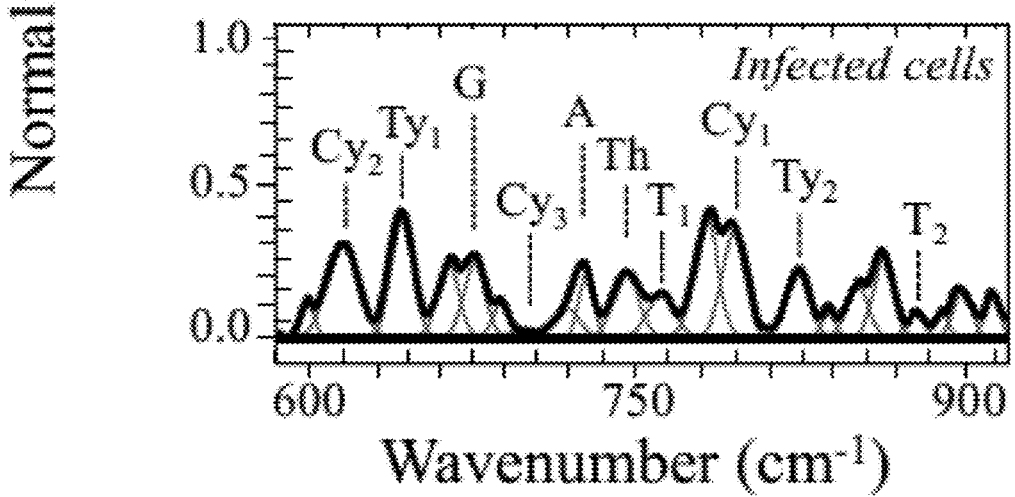
Figure 5F:
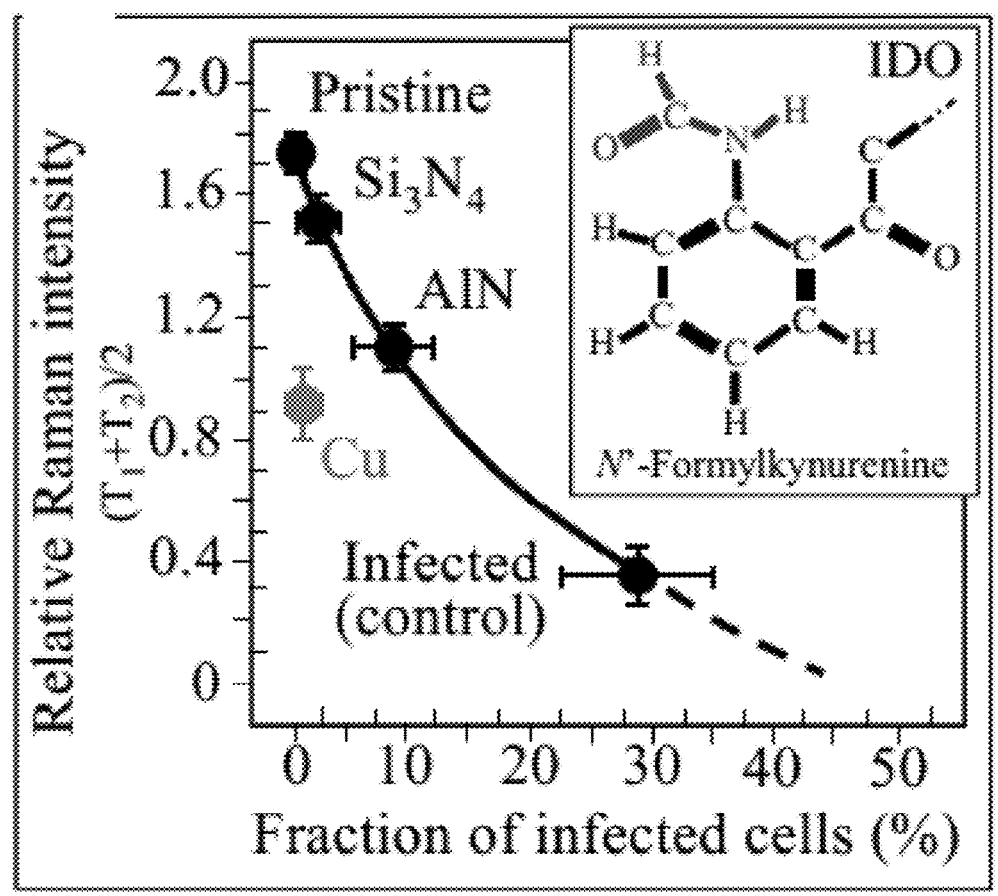
Figure 5G:
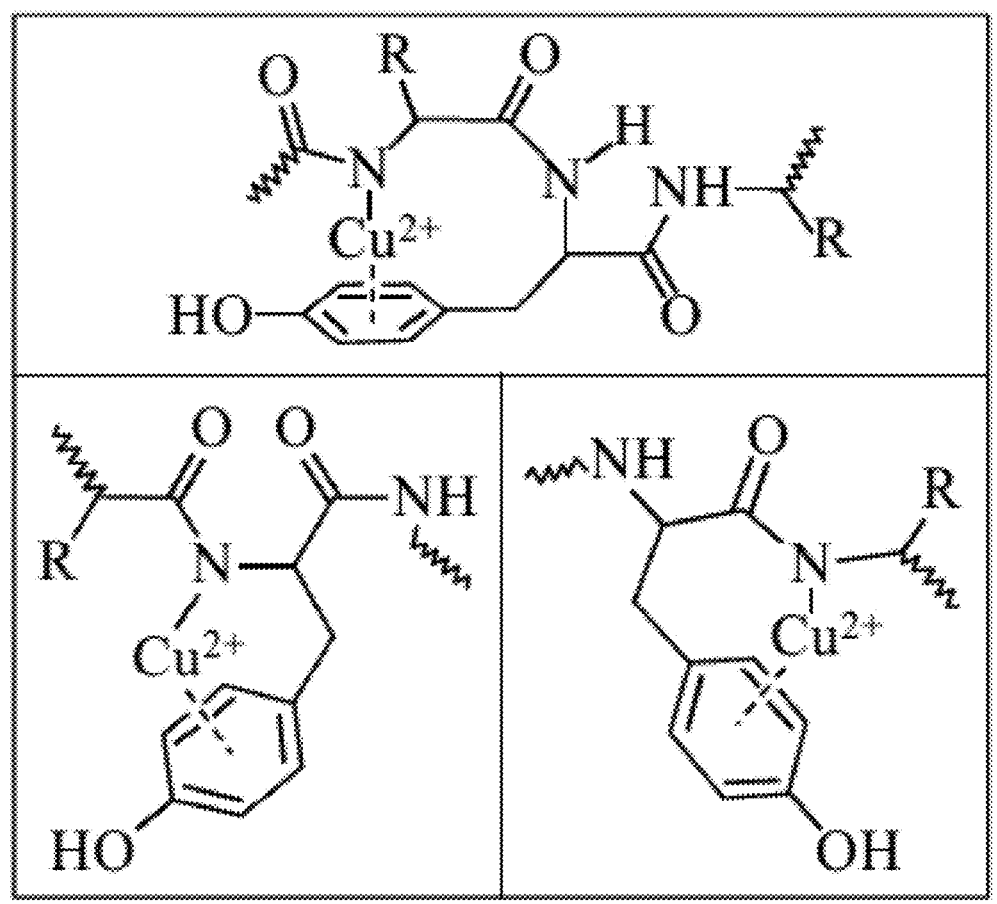

Raman spectroscopy examined VeroE6 cells exposed to the various supernatants to assess biochemical cellular changes due to infection and ionic (i.e., Cu and Al) toxicity. FIGS. 5A-5G show Raman spectra in the frequency range 700-900 cm-1 for (a) uninfected VeroE6/TMPRSS2 cells, and cells inoculated with supernatants containing virions exposed for 10-minutes to (b) $Si_3N_4$, (c) AlN, (d) Cu (positive control), and (e) no antiviral compounds (negative control). Of fundamental importance are the vibrational bands of ring breathing and H-scissoring of the indole ring of tryptophan (at 756 and 875 cm-1, labeled as T1 and T2, respectively). Tryptophan plays a vital role in protein synthesis and the generation of molecules for various immunological functions. Its stereoisomers serve to anchor proteins within the cell membrane and its catabolites possess immunosuppressive functions. The catabolism of tryptophan is triggered by a viral infection. This occurs via the enzymatic activity of indoleamine-2,3-dioxygenase (IDO) which protects the host cells from an over-reactive immune response. IDO reduces tryptophan to kynurenine and then to N'-formyl-kynurenine. An increase in IDO activity depletes tryptophan. Consequently, the intensity of the tryptophan bands (T1 and T2) is an indicator of these biochemical changes. Except for the Cu-treated sample, the data presented in FIG. 5F show an exponential decline in the combined tryptophan bands that correlates with the fraction of infected cells. (The chemical structure of N'-formyl-kynurenine is given in the inset for clarity.) The anomaly for copper provides further evidence of its toxicity. The VeroE6 cells consumed tryptophan to reduce $Cu^{2+}$ and stabilize it as $Cu^+$.

The Raman signals due to ring-stretching vibrations of adenine, cytosine, guanine, and thymine were found at 725, 795, 680, and 748 cm-1, and are labeled as A, Cy1, G, and Th, respectively, in FIGS. 5A-5E). These bands were preserved after virus exposure. However, there was an anomaly for lines representative of tyrosine at 642 and 832 cm-1 labeled as Ty1 and Ty2, respectively for cells infected with Cu-exposed virions. The ring-breathing band Ty2 of tyrosine was very weak compared to the other samples (cf. FIG. 5D with FIG. 5B). Conversely, the C—C bond-related Ty1 signal remained strong. This suggests that the aromatic ring of tyrosine chelated the Cu ions. This explains why only the tyrosine ring-breathing mode was reduced while the C—C signal remained unaltered. Three possible Cu(II) chelating conformations in tyrosine are given in FIG. 5G.

For VeroE6 cells exposed to virions treated with AlN (FIG. 5C), the tryptophan T1 and T2 bands were preserved, but the bands at 615 and –700 cm-1 due to ring bending in DNA cytosine (labeled as Cy2 and Cy3, respectively, in FIGS. 5A-5E) almost vanished. Their disappearance is due to either progressive internucleosomal DNA cleavage or from the formation of complexes, and both are related to toxicity. The loss of the cytosine signals is interpreted as a toxic effect by Al ions, although it is far less critical than copper. $Al_3^+$ interacts with carbonyl O and/or N ring donors in nucleotide bases and selectively binds to the backbone of the PO2 group and/or to the guanine N-7 site of the G-C base pairs by chelation.

Unlike exposure of the VeroE6 cells to Cu and AlN supernatants, which resulted in moderate to severe toxicity, $Si_3N_4$ invoked no modifications of tryptophan, tyrosine, and cytosine. The morphology of the spectrum for the $Si_3N_4$ viral supernatant closely matched that of the uninfected sham suspension (cf. FIGS. 5A and 5B).

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method for inactivating a human virus, the method comprising contacting the virus with an object comprising a powder comprising silicon nitride at a concentration from about 1 wt. % to about 30 wt. %, wherein the powder has an average particle size of 0.6 μm to 5 μm, wherein the silicon nitride successively binds and inactivates at least 99% of the virus, and wherein the object is a protective gown, a body cover, a head cover, a shoe cover, a face mask, a face shield, an eye protector, gloves, a surgical gown, a surgical drape, a cubicle curtain, a face mask filter, a respirator filter, an air filtration filter, an air ventilation filter, a knob, a handle, a railing, a bed frame, a bed tray, a table, a chair, an equipment rack, a cabinet, or a cart wherein the virus is not SARS-CoV-2.

2. The method of claim 1, wherein the silicon nitride is incorporated into or is present as a coating on a surface of the object.

3. The method of claim 1, wherein the object further comprises paper, cardboard, fabric, plastic, ceramic, stainless steel, metal, or a combination thereof.

4. The method of claim 1, wherein the object is in contact with the virus for at least one minute.

5. The method of claim 1, wherein at least 75% of the virus is inactivated after contact with the object.

6. The method of claim 1, wherein at least 99% of the virus is inactivated after contact with the object for at least 1 minute.

7. A method for inactivating a human virus, the method comprising contacting the virus with a composition comprising a powder comprising silicon nitride at a concentration from about 1 wt. % to about 30 wt. %, wherein the powder has an average particle size of 0.6 µm to 5 µm, wherein the silicon nitride successively binds and inactivates at least 99% of the virus wherein the virus is not SARS-CoV-2.

8. The method of claim 7, wherein the composition comprises a slurry, suspension, gel, paint, or toothpaste.

9. The method of claim 7, wherein the composition is a slurry that is sprayed onto a high-contact surface.

10. An article of personal protective equipment (PPE) having antiviral properties, the article comprising a powder comprising silicon nitride at a concentration from about 1 wt. % to about 30 wt. % embedded in or coated onto a surface of the article, wherein the powder has an average particle size of 0.6 µm to 5 µm, wherein the silicon nitride binds and inactivates at least 99% of a human virus wherein the virus is not SARS-CoV-2.

11. The article of claim 10, which is a body cover, a head cover, a shoe cover, a face mask, a face and eye protector, or gloves.

12. The article of claim 10, wherein the article is operable to inactivate the virus when the article contacts the virus for at least 1 minute.

* * * * *

UNITED STATES PATENT AND TRADEMARK OFFICE
CERTIFICATE OF CORRECTION

| | |
|---|---|
| PATENT NO. | : 11,844,344 B2 |
| APPLICATION NO. | : 17/230395 |
| DATED | : December 19, 2023 |
| INVENTOR(S) | : Bryan J. McEntire et al. |

It is certified that error appears in the above-identified patent and that said Letters Patent is hereby corrected as shown below:

On the Title Page

In the Title Item (54), delete "SARS-COV-2".
Insert --A VIRUS-- following 'OF'.

In the Specification

In the Title, Column 1, Line 2, delete "SARS-COV-2".
Insert --A VIRUS-- following 'OF'.

Signed and Sealed this
Twentieth Day of February, 2024

Katherine Kelly Vidal
*Director of the United States Patent and Trademark Office*